United States Patent
Nash et al.

(10) Patent No.: US 10,575,905 B2
(45) Date of Patent: Mar. 3, 2020

(54) AUGMENTED REALITY DIAGNOSIS GUIDANCE

(71) Applicant: Zimmer, Inc., Warsaw, IN (US)

(72) Inventors: Seth Anderson Nash, Fort Wayne, IN (US); John R. White, Winona Lake, IN (US); Annelise Galloway, Winona Lake, IN (US); Jody L. Claypool, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/919,139

(22) Filed: Mar. 12, 2018

(65) Prior Publication Data
US 2018/0256258 A1 Sep. 13, 2018

Related U.S. Application Data

(60) Provisional application No. 62/470,819, filed on Mar. 13, 2017, provisional application No. 62/470,690, filed on Mar. 13, 2017.

(51) Int. Cl.
*A61B 34/10* (2016.01)
*G06T 19/00* (2011.01)

(52) U.S. Cl.
CPC ............ *A61B 34/10* (2016.02); *G06T 19/006* (2013.01); *A61B 2034/104* (2016.02); *A61B 2034/108* (2016.02)

(58) Field of Classification Search
CPC ........ A61B 2034/104; A61B 2034/105; A61B 2034/108; A61B 2090/365;
(Continued)

(56) References Cited

U.S. PATENT DOCUMENTS 5,610,811 A 3/1997 Honda
6,701,174 B1 3/2004 Krause et al.
(Continued)

FOREIGN PATENT DOCUMENTS

EP 2618313 B1 7/2014
WO WO-2005084570 A1 9/2005
(Continued)

OTHER PUBLICATIONS

"International Application Serial No. PCT/US2017/051312, International Search Report dated Feb. 5, 2018", 7 pgs.
(Continued)

*Primary Examiner* — Chante E Harrison
(74) *Attorney, Agent, or Firm* — Schwegman Lundberg & Woessner, P.A.

(57) ABSTRACT

Systems and methods for using an augmented reality device during patient diagnosis. A method may include capturing an image of a patient, and presenting using an augmented reality display, while permitting the patient to be viewed through the augmented reality display, a virtual feature corresponding to anatomy of the patient obtained from the image. The method may include detecting impingement of the anatomy of the patient based on the image and displaying on the augmented reality display, an indication of the impingement at the virtual feature, such as by changing an attribute of the virtual feature.

19 Claims, 13 Drawing Sheets

(58) Field of Classification Search
CPC . A61B 2090/372; A61B 90/37; A61B 90/261; A61B 34/10; A61B 34/20; A61B 34/25; G02B 27/017; G06N 3/00; G06T 19/006; G16H 50/50; G16H 30/20; G16H 50/20; G06F 3/0484

See application file for complete search history.

(56) References Cited

U.S. PATENT DOCUMENTS

| | | | |
|---|---|---|---|
| 7,383,073 | B1 | 6/2008 | Abovitz et al. |
| 8,100,133 | B2 | 1/2012 | Mintz et al. |
| 8,600,478 | B2 | 12/2013 | Verard et al. |
| 8,884,618 | B2 | 11/2014 | Mahfouz |
| 9,105,207 | B2 | 8/2015 | Leung |
| 9,248,000 | B2 | 2/2016 | Sarvestani et al. |
| 9,492,240 | B2 | 11/2016 | Itkowitz et al. |
| 9,538,962 | B1 | 1/2017 | Hannaford et al. |
| 9,665,960 | B1 | 5/2017 | Masters et al. |
| 9,718,190 | B2 | 8/2017 | Larkin et al. |
| 9,836,654 | B1 | 12/2017 | Alvi et al. |
| 9,847,044 | B1 | 12/2017 | Foster |
| 9,892,564 | B1 | 2/2018 | Cvetko et al. |
| 9,898,664 | B2 | 2/2018 | Matsuzaki |
| 10,008,017 | B2 | 6/2018 | Itkowitz et al. |
| 10,235,807 | B2 | 3/2019 | Thomas et al. |
| 2002/0163499 | A1 | 11/2002 | Sauer |
| 2004/0044295 | A1 | 3/2004 | Reinert et al. |
| 2004/0046711 | A1 | 3/2004 | Triebfuerst |
| 2006/0043179 | A1 | 3/2006 | Nycz et al. |
| 2006/0142657 | A1 | 6/2006 | Quaid et al. |
| 2006/0142739 | A1 | 6/2006 | Disilestro et al. |
| 2007/0249967 | A1* | 10/2007 | Buly .............. A61B 5/1121 600/595 |
| 2008/0200926 | A1 | 8/2008 | Verard et al. |
| 2009/0017430 | A1 | 1/2009 | Muller-Daniels et al. |
| 2010/0159434 | A1 | 6/2010 | Lampotang et al. |
| 2010/0311028 | A1 | 12/2010 | Bell, III et al. |
| 2011/0093087 | A1* | 4/2011 | Mcmahon ............ A61F 2/34 623/22.42 |
| 2012/0075343 | A1 | 3/2012 | Chen et al. |
| 2013/0191099 | A1 | 7/2013 | Krekel |
| 2013/0267838 | A1 | 10/2013 | Fronk et al. |
| 2014/0081659 | A1 | 3/2014 | Nawana et al. |
| 2014/0188240 | A1* | 7/2014 | Lang .............. A61F 2/30942 623/22.12 |
| 2014/0272866 | A1 | 9/2014 | Kim |
| 2014/0275760 | A1 | 9/2014 | Lee et al. |
| 2015/0366628 | A1 | 12/2015 | Ingmanson |
| 2016/0089153 | A1 | 3/2016 | Couture et al. |
| 2016/0106554 | A1 | 4/2016 | Lavallee |
| 2016/0154620 | A1 | 6/2016 | Tsuda |
| 2016/0191887 | A1 | 6/2016 | Casas |
| 2016/0225192 | A1 | 8/2016 | Jones et al. |
| 2016/0228193 | A1 | 8/2016 | Moctezuma de la Barrera |
| 2016/0249989 | A1 | 9/2016 | Devam et al. |
| 2016/0324580 | A1 | 11/2016 | Esterberg |
| 2017/0027651 | A1 | 2/2017 | Esterberg |
| 2017/0202630 | A1 | 7/2017 | Gerstner |
| 2017/0258526 | A1* | 9/2017 | Lang ................ A61B 34/74 |
| 2017/0312031 | A1 | 11/2017 | Amanatullah et al. |
| 2017/0312032 | A1 | 11/2017 | Amanatullah et al. |
| 2017/0337402 | A1 | 11/2017 | Todeschini |
| 2017/0360513 | A1 | 12/2017 | Amiot et al. |
| 2018/0021097 | A1 | 1/2018 | Quaid et al. |
| 2018/0071032 | A1 | 3/2018 | De Almeida |
| 2018/0082480 | A1 | 3/2018 | White et al. |
| 2018/0090029 | A1 | 3/2018 | Fisher et al. |
| 2018/0098813 | A1 | 4/2018 | Nesichi et al. |
| 2018/0116823 | A1* | 5/2018 | Johannaber ......... A61B 5/0031 |
| 2018/0256256 | A1* | 9/2018 | May .................. G06T 19/003 |
| 2019/0038362 | A1 | 2/2019 | Nash et al. |

FOREIGN PATENT DOCUMENTS

| | | |
|---|---|---|
| WO | WO-2016133644 A1 | 8/2016 |
| WO | 2018052966 | 3/2018 |
| WO | WO-2018169891 A1 | 9/2018 |
| WO | WO-2018052966 A8 | 10/2018 |

OTHER PUBLICATIONS

"International Application Serial No. PCT/US2017/051312, Invitation to Pay Add'l Fees and Partial Search Rpt dated Dec. 8, 2017", 15 pgs.

"International Application Serial No. PCT/US2017/051312, Written Opinion dated Feb. 5, 2018", 13 pgs.

Stefl, M., et al., "Spinopelvic mobility and acetabular component position for total hip arthroplasty", Bone Joint J 2017;99-B(1 Supple A):37-45., (2017), 9 pgs.

"U.S. Appl. No. 15/703,239, Non Final Office Action dated Jun. 1, 2018", 17 pgs.

"International Application Serial No. PCT US2018 022074, International Search Report dated Jun. 6, 2018", 8 pgs.

"International Application Serial No. PCT US2018 022074, Written Opinion dated Jun. 6, 2018", 10 pgs.

"U.S. Appl. No. 15/703,239, Final Office Action dated Nov. 8, 2018", 24 pgs.

"U.S. Appl. No. 15/703,239, Response filed Jan. 8, 2019 to Final Office Action dated Nov. 8, 2018", 11 pgs.

Delp, Scott L, et al., "Surgical Simulation: An Emerging Technology for Training in Emergency Medicine", Presence: Teleoperators and Virtual Environments 6:2; 147-159, (1997), 14 pgs.

"U.S. Appl. No. 15/703,239, Response Filed Aug. 31, 2018 to Non-Final Office Action dated Jun. 1, 2018", 11 pgs.

"U.S. Appl. No. 15/703,239, Advisory Action dated Jan. 30, 2019", 4 pgs.

"U.S. Appl. No. 15/703,239, Response filed Feb. 8, 2019 to Final Office Action dated Nov. 8, 2018", 13 pgs.

"International Application Serial No. PCT/US2017/051312, International Preliminary Report on Patentability dated Mar. 28, 2019", 15 pgs.

U.S. Appl. No. 16/040,951, filed Jul. 20, 2018, Surgical Field Camera System.

"U.S. Appl. No. 15/703,239, Non Final Office Action dated June 19, 2019", 33 pgs.

"U.S. Appl. No. 15/703,239, Response filed Sep. 19, 2019 to Non-Final Office Action dated Jun. 19, 2019", 13 pgs.

"International Application No. PCT US2018 022074, International Preliminary Report on Patentability dated Sep. 26, 2019", 12 pgs.

* cited by examiner

US 10,575,905 B2

AUGMENTED REALITY DIAGNOSIS GUIDANCE

CLAIM OF PRIORITY

This application claims the benefit of priority to U.S. Provisional Application Ser. No. 62/470,819, filed Mar. 13, 2017, titled "Augmented Reality Diagnosis Guidance" and U.S. Provisional Application Ser. No. 62/470,690, filed Mar. 13, 2017, titled "Augmented Reality Surgical Technique Guidance" which are hereby incorporated herein by reference in their entirety.

BACKGROUND

Diagnostics are used to evaluate a patient to determine whether the patient needs a surgical procedure, such as a total hip arthroplasty, ligament repair, knee replacement, or the like. These procedures are performed hundreds of thousands of times a year in the United States. Surgical advancements have allowed surgeons to use preoperative planning, display devices, and imaging, to improve diagnoses and surgical outcomes. While these advances have allowed for quicker and more successful diagnoses, these diagnostic techniques are highly technical and difficult for patients to understand.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods for using an augmented reality device for diagnosis are described herein. The systems and methods herein describe uses for the augmented reality device, such as to display virtual components or representations of real objects overlaid on a real environment. An augmented reality (AR) device allows a user to view displayed virtual objects that appear to be projected into the real environment, which is also visible. AR devices typically include two display lenses or screens, including one for each eye of a user. Light is permitted to pass through the two display lenses such that aspects of the real environment are visible while also projecting light to make virtual elements visible to the user of the AR device.

An AR device includes an AR display which may be used to display a virtual component while allowing real objects to be viewed. The virtual component may include measurements, angles, an identification of an impingement (e.g., a femoroacetabular impingement) or a potential impingement, a representation of an implant, a representation of patient anatomy, a range of motion plane or axis, or the like. For example, alignment angles may be shown virtually on an image of a patient or on a virtually presented skeleton, for example overlaid on the patient, using the AR display.

Patient imaging may be performed (e.g., using a CT scan, an MIll, an X-ray, or the like) to create at least one patient image. In an example, two images may be used (e.g., two-dimensional images) to create a three-dimensional representation of an aspect of a patient's anatomy. The three-dimensional representation may be displayed virtually using an AR display. When displayed virtually, the three-dimensional representation may be manipulated or observed in the AR display (e.g., rotated, moved, zoomed in or out on, virtually cut, etc.).

Two or more AR devices may be used in a coordinated manner, for example with a first AR device controlling one or more additional AR devices, or in a system with defined roles. For example, when activating an AR device, a user may select a role (e.g., clinician or patient) and the AR device may display information relevant to that role. For example, the AR display for a clinician may include more information or more complex or technical information than the AR display for a patient, which may be simplified for ease of understanding. In an example, the clinician AR device may control what is viewed on the patient AR device.

Figure 1:
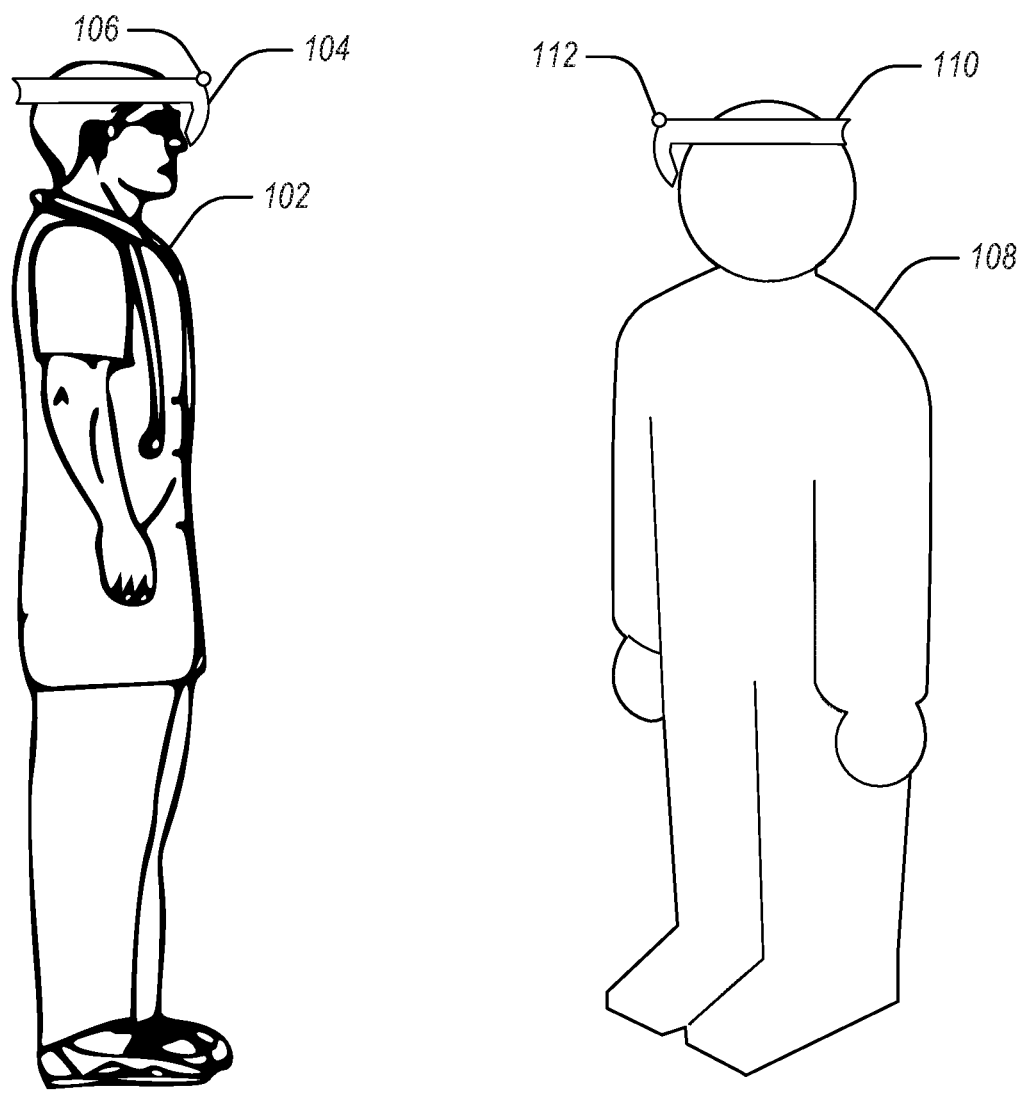
FIG. 1 illustrates a clinician and a patient using augmented reality in accordance with some embodiments.

FIG. 1 illustrates a clinician 102 and a patient 108 using augmented reality in accordance with some embodiments. The clinician is wearing an augmented reality (AR) device 104 which may be used to display a virtual object to the clinician 102. The virtual object may not be visible to others if they are not wearing an AR device. Even if another person (e.g., the patient 108) is using an AR device (e.g., the AR device 110, which may have a camera 112), the person may not be able to see the virtual object. In another example, the patient 108 may be able to see the virtual object in a shared augmented reality with the clinician 102, or may be able to see a modified version of the virtual object (e.g., according to customizations unique to the clinician 102 or the patient 108). Augmented reality is explained in more detail below.

Augmented reality is a technology for displaying virtual or "augmented" objects or visual effects overlaid on a real environment. The real environment may include a room or specific area, or may be more general to include the world at large. The virtual aspects overlaid on the real environment may be represented as anchored or in a set position relative to one or more aspects of the real environment. For example, a virtual object may be configured to appear to be resting on a table. An AR system may present virtual aspects that are fixed to a real object without regard to a perspective of a viewer or viewers of the AR system (e.g., the clinician 102). For example, the virtual object may exist in a room, visible to a viewer of the AR system within the room and not visible to a viewer of the AR system outside the room. The virtual object in the room may be displayed to the viewer outside the room when the viewer enters the room. In this example, the room may act as a real object that the virtual object is fixed to in the AR system.

The AR device 104 may include one or more screens, such as a single screen or two screens (e.g., one per eye of a user). The screens may allow light to pass through the screens such that aspects of the real environment are visible while displaying the virtual object. The virtual object may be made visible to the clinician 102 by projecting light. The virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects may be fixed to a real object or area in both views. Aspects such as a color of an object, lighting, or other changes may be made among the views without changing a fixed position of at least one virtual object.

A user may see the virtual object presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object (e.g., using one or more cameras, which may be mounted on an AR device, such as AR device camera 106 or separate, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). An AR device 104 may include a camera 106 on the AR device 104. The AR device camera 106 may include an infrared camera, an infrared filter, a visible light filter, a plurality of cameras, a depth camera, etc. The AR device 104 may project virtual items over a representation of a real environment, which may be viewed by a user. The clinician 102 may control a virtual object using the AR device 104, a remote controller for the AR device 104, or by interacting with the virtual object (e.g., using a hand to "interact" with the virtual object or a gesture recognized by the camera 106 of the AR device 104).

The AR device 104 and the AR device 110 may be part of a shared AR system. The shared AR system may allow the AR devices to view the same or similar content, to be in communication with each other, for one to control the other, or the like. For example, the clinician 102 may control the AR device 110 of the patient 108 using the clinician's own AR device 104 (e.g., using a remote, a gesture, a button on the AR device 104, or the like). In an example, the clinician 102 and the patient 108 may select their respective roles when initiating the AR devices 104 and 110 respectively.

By assigning roles to the AR devices, the AR devices may automatically provide appropriate virtual objects to be displayed. For example, the clinician 102 may select the clinician role for the AR device 104. Once the clinician role is selected, the clinician 102 may be presented with a plurality of choices for display, such as diagnostic tools, viewing imaging of the patient 108, selecting a patient file, education information, or the like. When the clinician 102 selects a choice, the AR device 104 may display virtual objects or information corresponding to the choice. In an example, the AR device 110 may automatically display virtual objects or information (which may correspond to the choice, to the clinician-displayed virtual objects or information, or may be derived from the choice or the clinician-displayed virtual objects or information) for view by the patient 108. For example, the clinician 102 may choose to view an image of a bone of the patient 108. The image may be previously obtained. The AR device 104 may display, in response to the choice, a three-dimensional view of the bone, and for example, additional clinical information (e.g., technical data). The AR device 110 may automatically display, in response to the choice a three-dimensional view of the bone without the additional clinical information or with basic educational information (e.g., labels for names of parts of the bone). In an example, the clinician 102 may manipulate the virtual representation of the bone (e.g., using a button or gesture to rotate or zoom the bone) and the changes to the bone may be automatically reflected in the AR device 110 of the patient 108.

The AR device 104 of the clinician 102 may automatically identify a bony impingement (e.g., using the camera 106 or by analyzing an image). A virtual representation of the impingement may be displayed (e.g., as a red virtually-highlighted area) using the AR device 104 or the AR device 110, for example on an image, presented on the patient 108 (e.g., with a three-dimensional skeletal overlay on the patient 108), or the like. The virtual representation of the impingement may move as the patient 108 moves, and may disappear or appear to fade away if the impingement is (temporarily) removed (e.g., if it is temporarily not present when the patient 108 sits or stands).

Figure 2A:
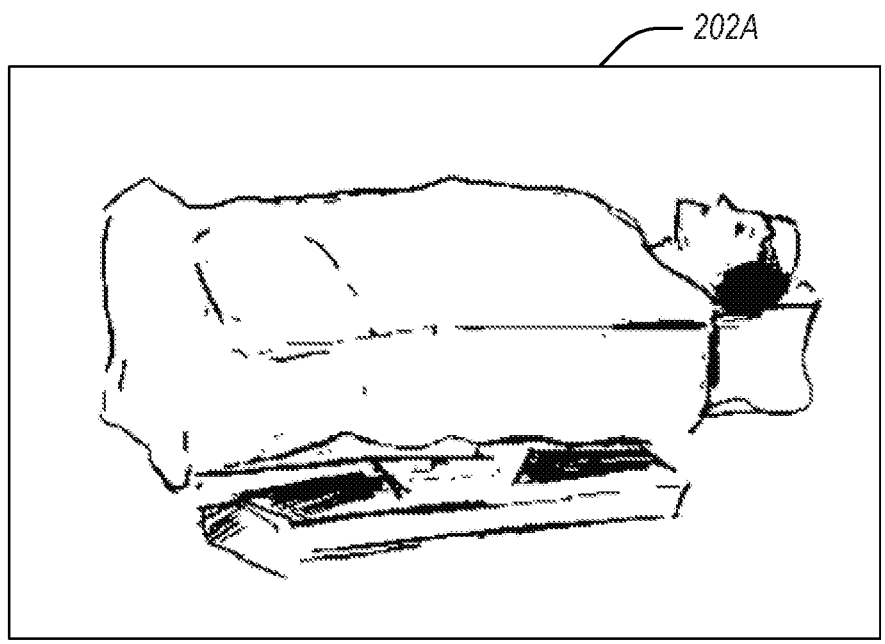
FIGS. 2A-2F illustrate diagnostic augmented reality displays in accordance with some embodiments.
Figure 2A:
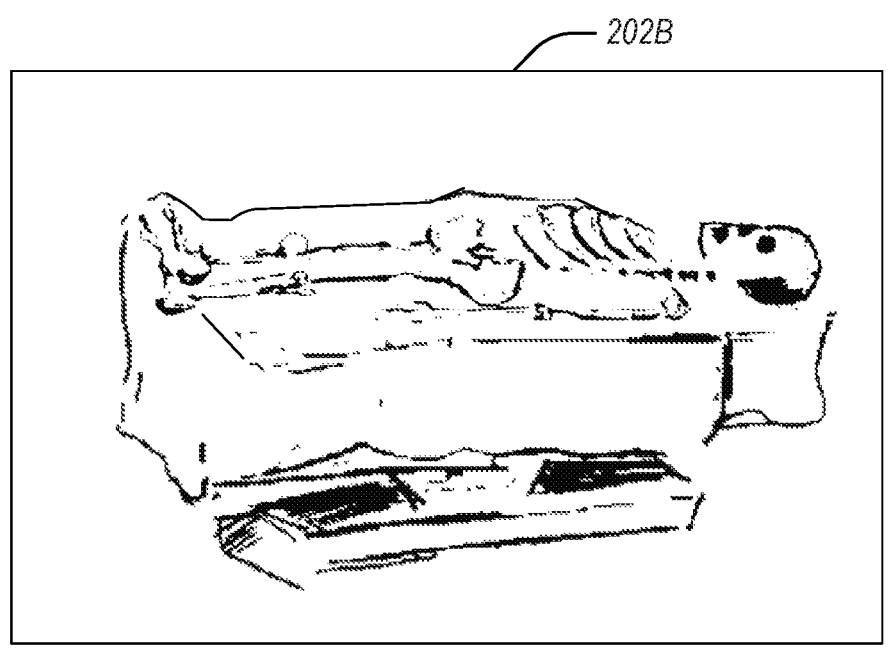

FIGS. 2A-2F illustrate diagnostic augmented reality displays in accordance with some embodiments. FIG. 2A illustrates a first view 202A of a patient without augmented or virtual components and a second view 202B of the patient with a virtual skeleton overlaid on the patient. The virtual skeleton may be based on imaging of the patient. For example, the skeleton may be created by using two images (e.g., X-rays) of the patient to create a three-dimensional model of the patient's skeleton, which may be displayed virtually using an AR display as shown in the second view 202B. In another example, the skeleton may be determined in real time from an image of the patient using a camera of an AR device that is then used to display the skeleton, based on a generic or template skeleton model scaled or deformed to fit the image of the patient taken by the AR device.

For example, one or more landmarks on the virtual skeleton may be associated with bony landmarks of the patient (such as at the knee joint). The landmarks may be identified and tracked by the AR device and used to align the virtual skeleton with the real-life moving patient anatomy. In an example, the one or more landmarks may be used to align and scale the virtual skeleton to the patient (e.g., a foot landmark, a head landmark, a hip landmark, a hand landmark, etc.). The landmarks may be identified using a registration device, such as a pointer or finger within an AR view. For example, a clinician may point to or touch each identified landmark to register the landmark to the patient. After registration, the virtual skeleton may be applied to the patient in the AR view. For example, a generic or template skeleton may be overlaid on the patient. In another example, a skeleton based on the two images (e.g., X-rays) may be used as a virtual skeleton. A clinician may toggle between the views using an AR device.

Figure 2B:
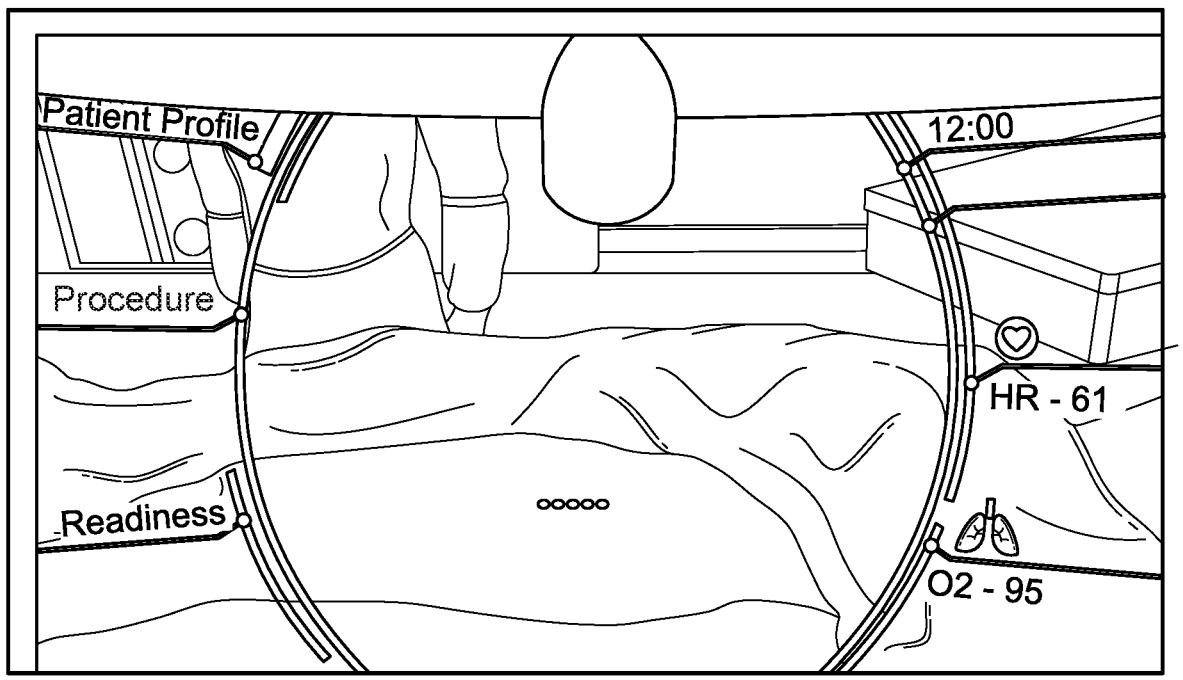

FIG. 2B illustrates an AR display 203 of a patient. The AR display 203 may include technical information displayed virtually, such as height, weight, BMI, co-morbidities (e.g., hypertension, cardiovascular disease, peripheral vascular disease, congestive heart failure, renal function impairment, diabetes, respiratory disease, etc.) for a patient being viewed through the AR display 203. The AR display 203 may include patient information (e.g., name, age, allergies, potential patient-specific complications, etc.), readiness information, time or counters, or the like. In an example, the AR display 203 may include virtually displayed diagnosis type information, such as information from a patient file, reported pain, any previously identified impingement, referral notes (e.g., from a general practitioner), family medical history information (e.g., parental impingement procedures or co-morbidities), or the like. In an example, the clinician may interact with the virtually displayed diagnosis type information, for example by zooming in or out, selecting the virtually displayed diagnosis type information (e.g., if additional information is available, such as a diagnosis recommendation), or the like. The displayed information may be accessed or changed in real time, including updating the information for display in the AR display 203. In an example, a clinician using the AR display 203 may change the information displayed, such as by using a gesture or input device, or may save the information or a snapshot of the AR display 203, such as to a patient file.

Figure 2C:
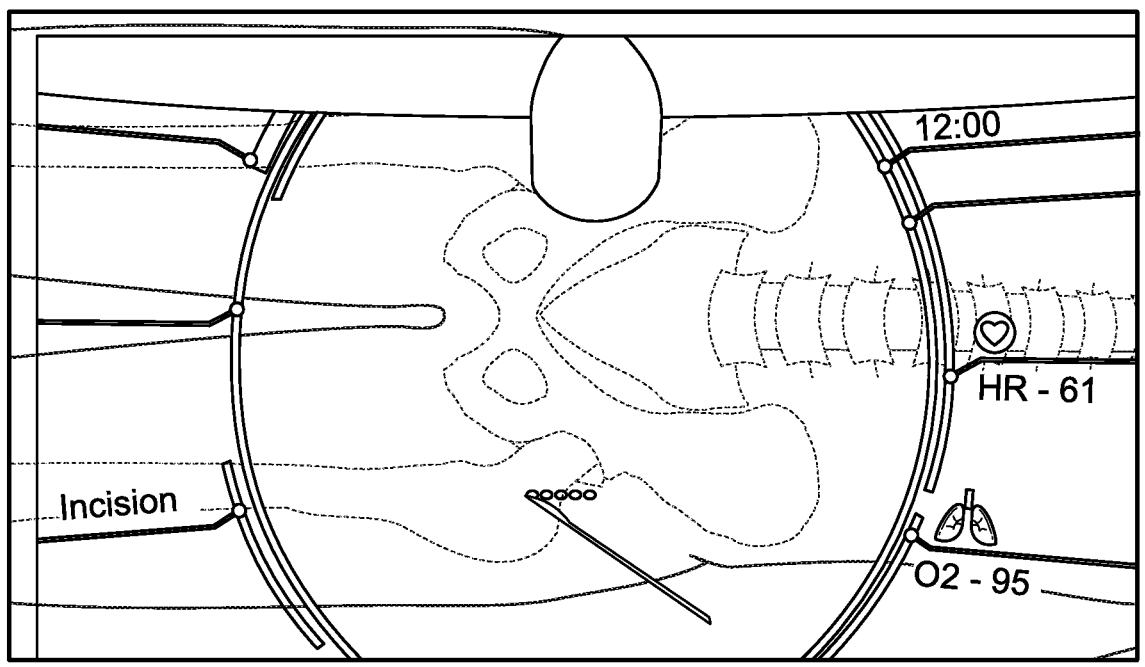

FIG. 2C illustrates an AR display 205 including a virtual skeleton overlaid on a patient. The AR display 205 may include aspects described above in relation to AR display 203. The virtual skeleton overlaid may be generated from an image of the patient or using a camera of an AR device including the AR display 205. The virtual skeleton may be virtually coupled to the patient, for example if the patient moves, then the skeleton may move accordingly.

Figure 2D:
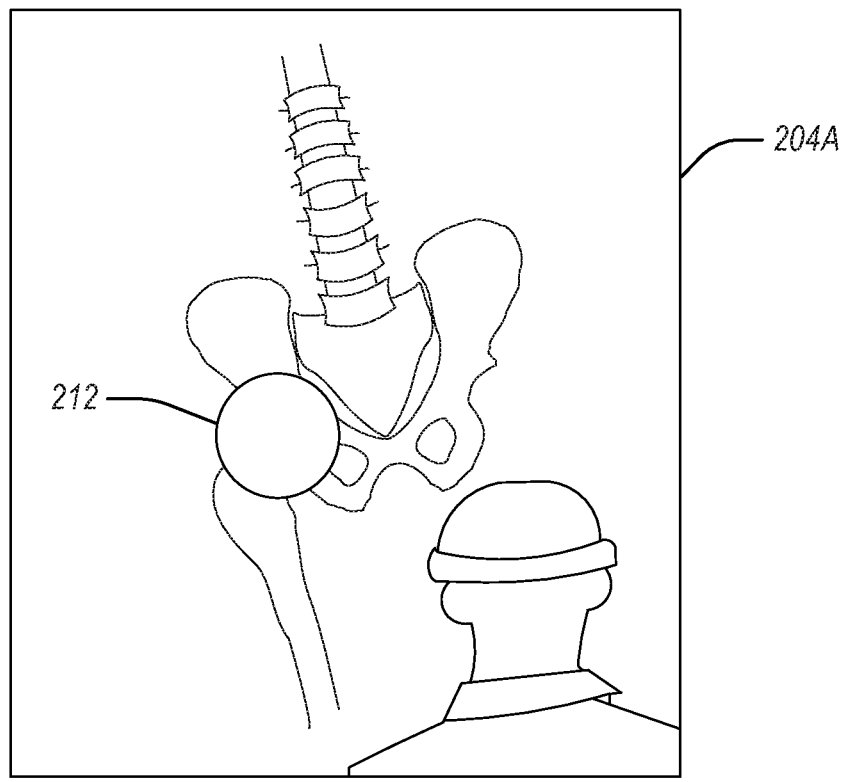
Figure 2D:
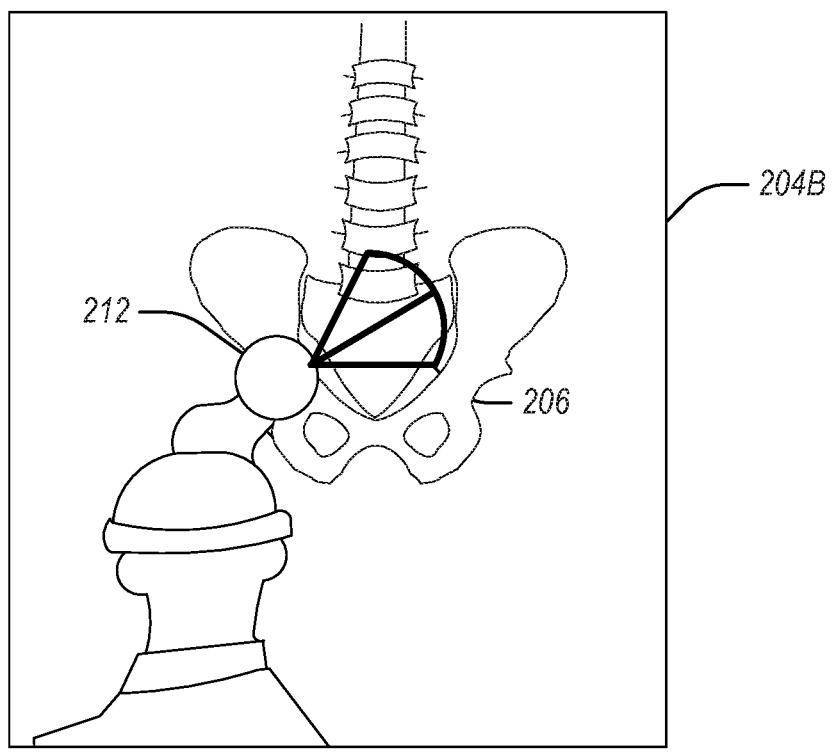

FIG. 2D illustrates an AR display presenting a first view 204A of a patient image and a second view 204B of the patient image. The first view 204A includes a virtually highlighted area 212 of an image or of a virtual representation of anatomy of a patient. The image may be obtained using x-ray, MRI, CT scan, or the like. The virtual representation may be a representation of an obtained image or may be a three-dimensional representation that may be created from, for example, two or more images used to create a three-dimensional model that may then be displayed virtually. The virtually highlighted area 212 may correspond with an impingement. The impingement may be identified from an image of anatomy of the patient or form virtually projected anatomy of the patient. For example, the impingement may be automatically identified and the virtually highlighted area 212 may be projected based on the automatic identification. The patient may report pain in an area, which may be evaluated for impingement.

In an example, a clinician may virtually view the anatomy (e.g., at least part of a skeleton) and identify an impingement or a potential impingement. In response to the clinician identifying the impingement or the potential impingement, the AR display may highlight the impingement or the potential impingement (e.g., in red) virtually (e.g., display the virtually highlighted area 212). The virtually displayed anatomy may be manipulated by the clinician (e.g., rotated, zoomed, moved, etc.). The manipulation may be performed using a gesture, a button (e.g., on a remote or on the AR device), or the like. The manipulation may allow the clinician to better identify the impingement. In an example, the clinician may manipulate a portion of the virtually displayed anatomy while leaving other portions of the virtually displayed anatomy static (or move other portions in a different direction relative to the first portion). For example, the clinician may cause a virtually displayed knee to bend or hip to swivel or shoulder to rotate. By viewing the movement of a bone in the virtually displayed anatomy relative to another bone, impingement may be detected by the clinician or automatically by the AR device (e.g., by identifying overlap in the virtually displayed anatomy). The impingement may then be displayed as the virtually highlighted area 212.

The second view 204B may include one or more virtual angles 206 or virtual lines used to indicate, for example, potential acetabular component position for a surgical intervention, an implant alignment, anatomy (e.g., bone, muscle, ligament, other soft tissue, or the like) or position, orientation, or location of anatomy, or may include Spinopelvic angles, described in more detail below with respect to FIG. 2E. The virtual angles 206 may be automatically detected and projected onto the image or virtual representation, for example using the highlighted portion as an origin location.

Figure 2E:
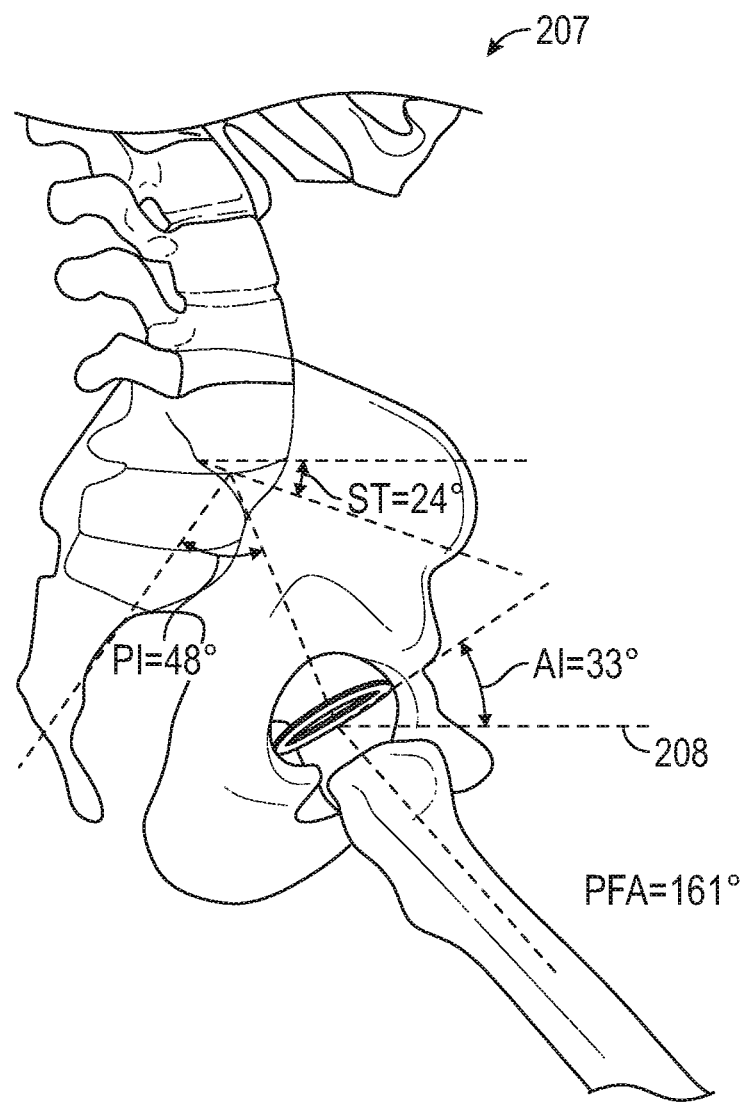

FIG. 2E illustrates an AR display 207 including one or more virtual angles 208. The virtual angles 208, referred to herein as Spinopelvic angles, are displayed virtually in the AR display 207. The Spinopelvic angles may include a pelvic incidence (PI), a sacral tilt (ST), a pelvic femoral angle (PFA), an anteinclination (AI) of the pre-operative acetabulum, and a sacral acetabular angle (SAA). The PI and SAA may be static numbers that are the same standing and sitting. The Spinopelvic angles are described in more detail in "Spinopelvic mobility and acetabular component position for total hip arthroplasty," *Bone Joint J* 2017; 99-B (1 Supple A):37-45, Stefl, et. al, which is hereby incorporated herein by reference in its entirety.

Figure 2F:
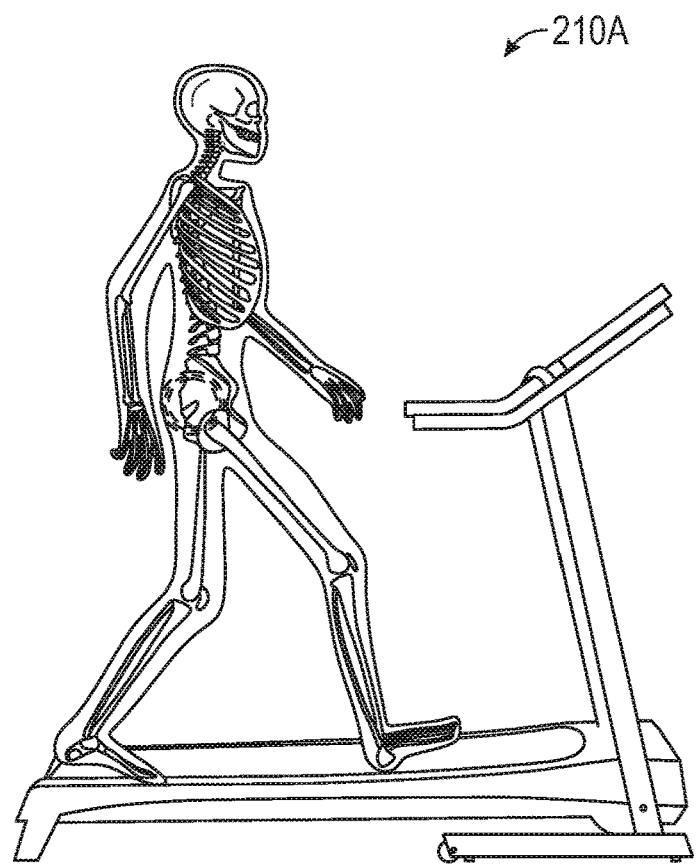
Figure 2F:
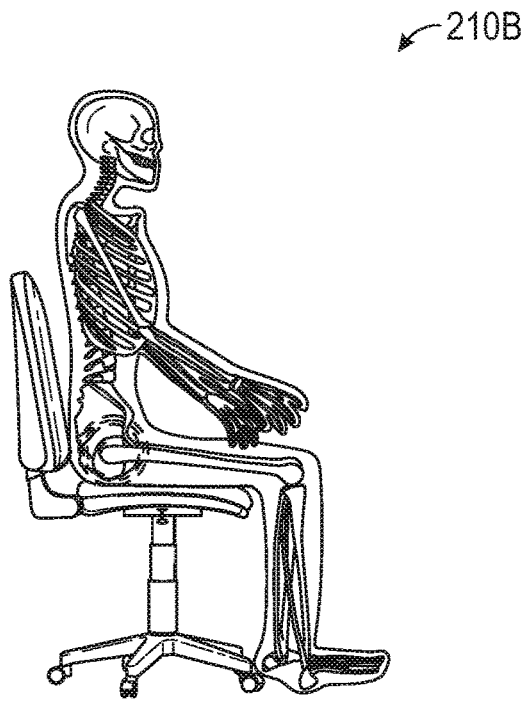

FIG. 2F illustrates a first AR display 210A and a second AR display 210B showing virtual components displayed in a real environment. The first AR display 210A includes a virtual component (e.g., an impingement or potential impingement) highlighted on a virtual skeleton of a patient walking on a treadmill. The second AR display 210B includes a virtual component (e.g., an impingement or potential impingement) highlighted on a virtual skeleton of a patient sitting on a chair. The virtual skeleton may be virtually coupled to the patient, for example if the patient moves, then the skeleton may move accordingly. Thus the first AR display 210A may allow a clinician to observe skeletal (or other anatomical aspects which may be displayed virtually) action when the patient walks, for example to examine range of motion, potential impingement, or other clinical analysis. The second AR display 210B may allow a clinician to make observations or an examination of the patient in a seated position. The impingement or potential impingement (the highlighted virtual component) of AR displays 210A or 210B may be detected automatically (e.g., using an AR device or a camera) or may be identified by a clinician. When detected automatically, the highlighting may be automatically applied, and when identified by the clinician, the highlighting may be applied in response to receiving input from the clinician indicating the identification.

Figure 3:
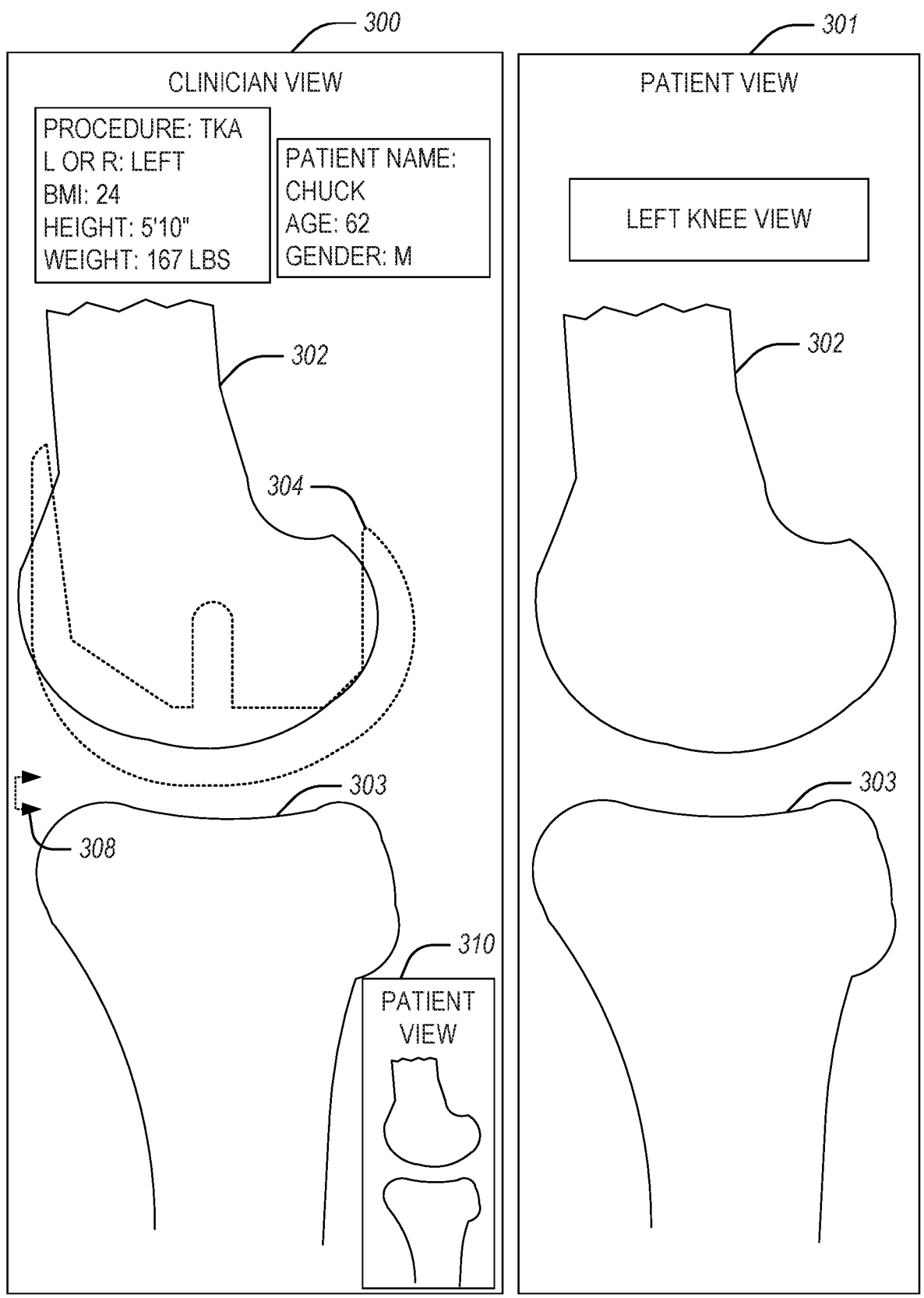
FIG. 3 illustrates a clinician augmented reality display and a patient augmented reality display in accordance with some embodiments.

FIG. 3 illustrates a clinician augmented reality display 300 and a patient augmented reality display 301 in accordance with some embodiments. The clinician AR display 300 includes virtually displayed information, and example virtually displayed components or augmented images. For example, bones 302 and 303 may be on a printed or screen-displayed image or may be virtually displayed. An implant or trial 304 may be displayed virtually on the bone 302. A gap 308 may be displayed for the clinician on the clinician AR display 300. The clinician AR display 300 may include a virtual representation 310 of the patient AR display 301. The patient AR display 301 includes a simplified version of the view available in the clinician AR display 300. For example, the bones 302 and 303 may be shown on the patient AR display 301 without additional comorbidity information, virtually displayed information, the implant or trial 304, the gap 308, etc.

The patient AR display 301 may be controlled by the clinician AR display 300. For example, the clinician may select aspects of the clinician AR display 300 to be shared with the patient AR display 301. In an example, the clinician may, for example drag aspects of the clinician AR display 300 onto the virtual representation 310 of the patient view. Dragged aspects may then be displayed on the patient AR display 301. In another example, the clinician may select a program or procedure which may then automatically display virtual components in the clinician AR display 300 or in the patient AR display 301.

Figure 4:
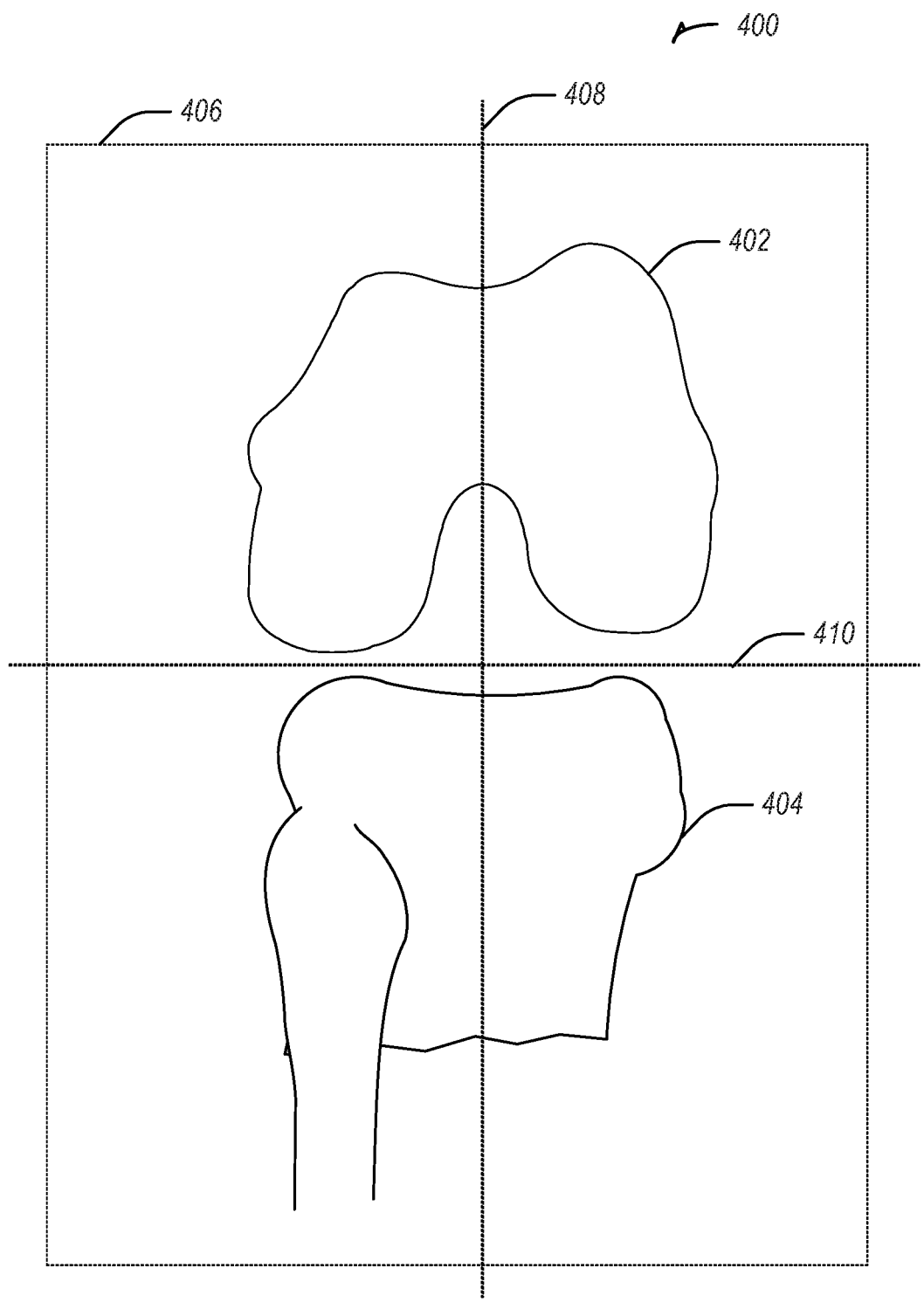
FIG. 4 illustrates a display including virtual range of motion components in accordance with some embodiments.

FIG. 4 illustrates an AR display 400 including virtual range of motion components in accordance with some embodiments. The AR display 400 includes a femur 402 and a tibia 404 for illustration purposes of a knee replacement, but other bones may be displayed (e.g., for a shoulder replacement or hip replacement). The AR display 400 may include one or more planes or axes, such as planes 406-410. The planes 406-410 may be used for range of motion tests. For example, plane 408 may be displayed for extension or flexion range of motion testing. The plane 408 may be displayed virtually for the range of motion test to be conducted while keeping the knee within the plane 408. Thus the planes 406-410 may be displayed virtually to guide a clinician in conducting a range of motion test.

Figure 5:
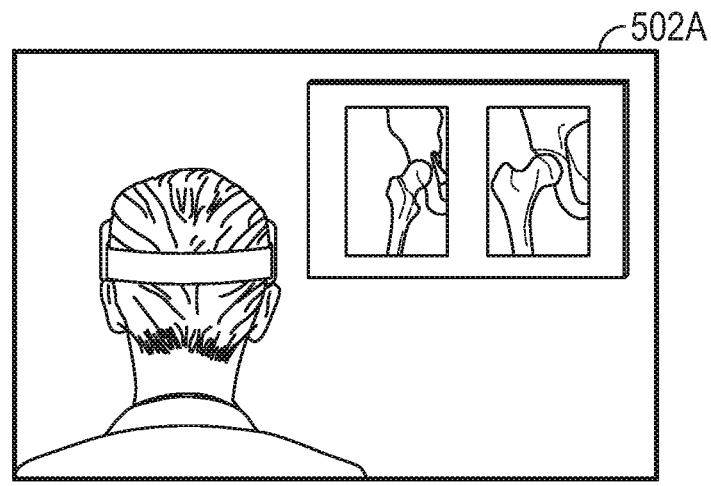
FIG. 5 illustrates a three dimensional rendering of a virtual component from two dimensional images in an augmented reality display in accordance with some embodiments.
Figure 5:
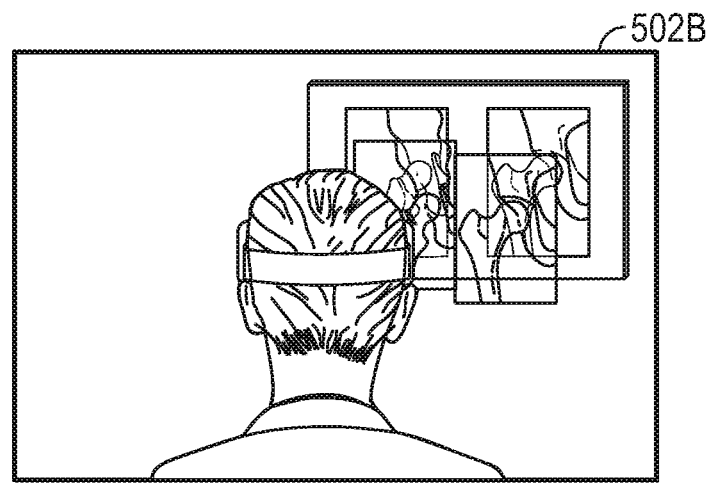
Figure 5:
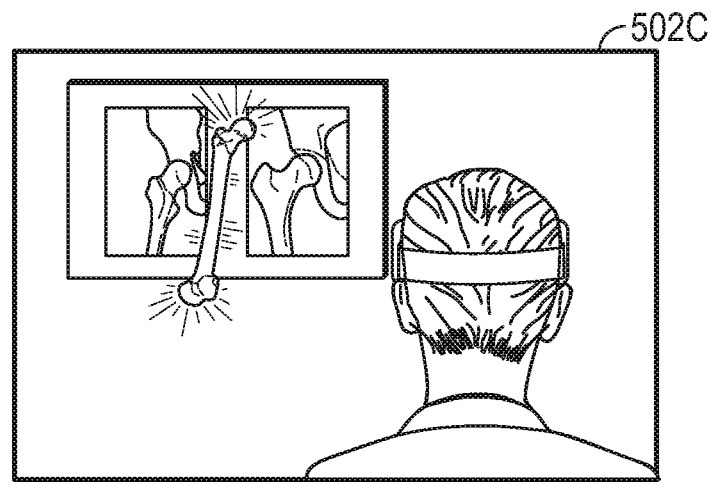

FIG. 5 illustrates a three dimensional rendering of a virtual component from two dimensional images in an augmented reality display in accordance with some embodiments. The AR display 502A includes two images that may be taken of anatomy of a patient, for example using an x-ray, an MRI, a CT scan, or the like. The images may be two-dimensional. The AR display 502A may not include virtual components. The AR display 502B may illustrate an animation to create a three-dimensional virtual representation of the patient anatomy (e.g., a bone) from the images. The AR display 502B illustrates a transition stage in the animation between the two-dimensional images displayed in the AR display 502A and the three-dimensional virtual representation illustrated in AR display 502C. The AR displays 502A-502C may represent three stages of an animation to create the three-dimensional virtual representation from the two-dimensional images. The AR display 502C illustrates the three-dimensional virtual representation of the patient anatomy. The three-dimensional virtual representation may be interacted with by a clinician viewing the AR display 502C, for example using a button, a remote, a gesture, etc. The interaction may manipulate the three-dimensional virtual representation, for example rotate, move, zoom, etc., the three-dimensional virtual representation. In an example, the virtual representation may be created using a 3D modeler running on a computer, such as that described in U.S. Publication Number 2013/0191099, titled "Process for generating a computer-accessible medium including information on the functioning of a joint," which is hereby incorporated by reference herein, in its entirety. By manipulating the three-dimensional virtual representation, the clinician may detect impingement or potential impingement. In response to receiving an indication from the clinician that impingement or potential impingement has been detected, the AR display 502C may illustrate, highlight, or otherwise display the impingement or potential impingement virtually. For example, the impingement or potential impingement may be highlighted in red. In another example, an impingement or potential impingement may be automatically detected, such as by virtually moving bones and detecting whether impingement has occurred. For example, two bones may be displayed and moved relative to one another, and a camera may be used to detect if there is overlap between the two bones. In yet another example, the bones may be automatically moved for the clinician to detect impingement or potential impingement.

Figure 6:
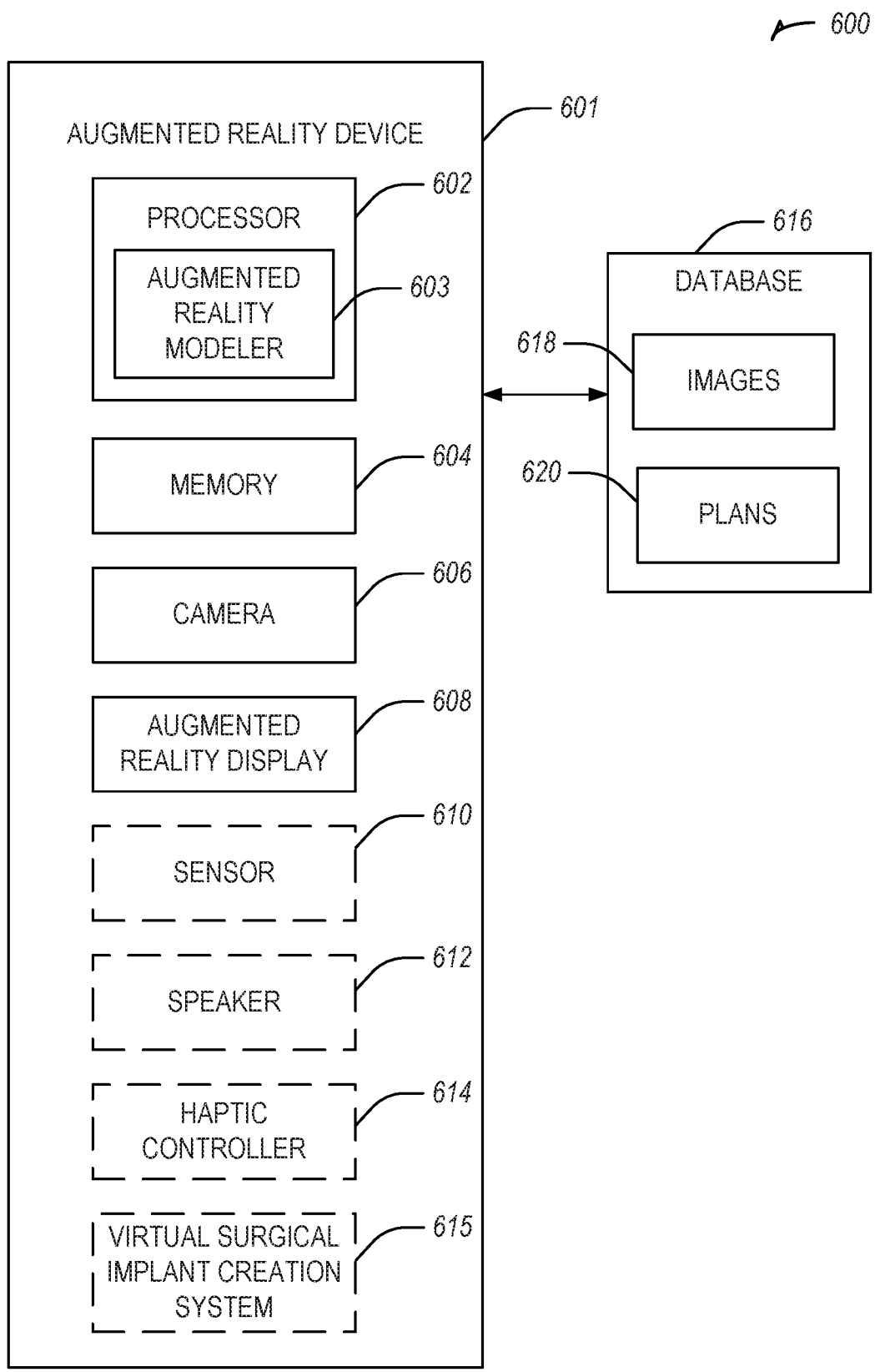
FIG. 6 illustrates a system for diagnosis using augmented reality in accordance with some embodiments.

FIG. 6 illustrates a system 600 for diagnosis using augmented reality in accordance with some embodiments. The system 600 may be used to perform the technique 700 described in relation to FIG. 7 below, for example, by using the processor 602. The system includes an augmented reality device 601 that may be in communication with a database 616. The augmented reality device 601 includes a processor 602, memory 604, an AR display 608, and a camera 606. The augmented reality device 601 may include a sensor 610, a speaker 612, or a haptic controller 614. The database 616 may include image storage 618 or preoperative plan storage 620. In an example, the augmented reality device 601 may be a HoloLens manufactured by Microsoft of Redmond, Wash.

The processor 602 of the augmented reality device 601 includes an augmented reality modeler 603. The augmented reality modeler 603 may be used by the processor 602 to create the augmented reality environment. For example, the augmented reality modeler 603 may receive dimensions of a room, such as from the camera 606 or sensor 610, and create the augmented reality environment to fit within the physical structure of the room. In another example, physical objects may be present in the room and the augmented reality modeler 603 may use the physical objects to present virtual objects in the augmented reality environment. For example, the augmented reality modeler 603 may use or detect a table present in the room and present a virtual object as resting on the table. The AR display 608 may display the AR environment overlaid on a real environment. The display 608 may show a virtual object, using the AR device 601, such as in a fixed position in the AR environment.

The augmented reality device 601 may include a sensor 610, such as an infrared sensor. The camera 606 or the sensor 610 may be used to detect movement, such as a gesture by a surgeon or other user, that may be interpreted by the processor 602 as attempted or intended interaction by the user with the virtual target. The processor 602 may identify an object in a real environment, such as through processing information received using the camera 606.

The AR display 608, for example during a surgical procedure, may present, such as within a surgical field while permitting the surgical field to be viewed through the augmented reality display, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like. The AR device 601 may include a virtual surgical implant creation system 615 to create an implant, for example based on an image. The implant may be displayed on the augmented reality display as a virtual component.

Figure 7:
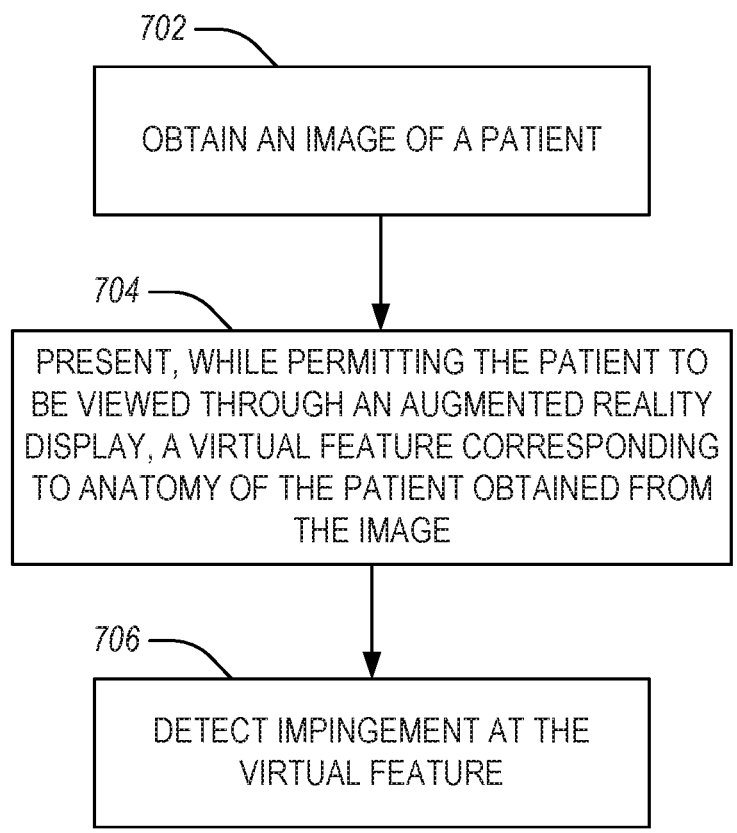
FIG. 7 illustrates a flow chart showing a technique for diagnosis using augmented reality in accordance with some embodiments.

FIG. 7 illustrates a flow chart showing a technique 700 for diagnosis using augmented reality in accordance with some embodiments. The technique 700 includes an operation 702 to obtain an image of a patient, for example by using an imaging device (e.g., in real time). The virtual feature may be created using two or more two dimensional images, for example as obtained by the imaging device.

The technique 700 includes an operation 704 to present, while permitting the patient to be viewed through an AR display, a virtual feature corresponding to anatomy of the patient obtained from the image. The virtual feature may include a bone or a set of bones, an implant, a skeletal model, for example presented overlaid on the patient, or the like. The skeleton may be configured to move when the patient moves (e.g., the virtual skeleton may be visually linked to the real anatomy of the patient).

The technique 700 may include an operation 706 to detect impingement at the virtual feature (e.g., of the anatomy of the patient). For example, the virtual feature may correspond to a bone of the patient and may be displayed virtually with other virtual bones. The bone may interact with one of the other virtual bones, indicating impingement. The impingement may be detected automatically, such as using a camera (e.g., by visually detecting the interaction using one or more images) or using a processor (e.g., by detecting the interaction from imaging data). In an example, the impingement may be identified by a clinician. The technique 700 may include receiving input from the clinician indicating the impingement. When the impingement is detected or the clinician input is received, the virtual feature or a portion of the virtual feature may be changed (e.g., highlighted, pulsed, flashed, changed color, etc.).

In an example, the technique 700 may include an operation to determine, such as from a plurality of images (which may be captured by the imaging device described above), that the anatomy of the patient has moved. In response to determining that the anatomy has moved, this operation may include determining that the impingement has resolved (e.g., there is no impingement in this orientation/configuration of the patient's anatomy, the anatomy is unimpinged, etc.), and in response to this determination, stop or pause display of an indication of the impingement at the virtual feature. In an example, instead of or in addition to stopping or pausing display of the indication, the operation may include showing the indication faded or offset from the virtual feature (e.g., to suggest that the impingement exists in the prior orientation/configuration but is not present in a current orientation/configuration).

The technique 700 may include an operation to present a plane or axis for orientation for performing a range of motion test on the patient. The technique 700 may include an operation to present one or more Spinopelvic angles corresponding to the virtual feature. The technique 700 may include an operation to create an implant, for example based on the image. In an example, the implant may be displayed on the augmented reality display as a virtual component.

The AR device may be used to communicate with a second AR device. The AR device may be used to control aspects of operation of the second AR device (e.g., what is displayed). In an example, the AR device may be a surgeon's device and the second AR device may be a patient's device. In an example, the patient sees less details in a display of the second AR device than the surgeon sees in the AR display of the AR device. In an example, when the surgeon adjusts, moves, or changes a virtual component displayed in the AR display, a corresponding virtual component displayed in a second AR display of the second AR device may be adjusted, moved, or changed accordingly. In an example, the technique 700 may include projecting a plane to allow the anatomy of the patient to be kept within the plane while performing a range of motion test (e.g., rotation, flexion, etc.). The plane may be used for any biomechanical measurement that is used in a diagnostic exam (e.g., extension or rotation in the shoulder, a scoliosis diagnosis, or the like).

In an example, the technique 700 may include outputting an indication of impingement (e.g., of the anatomy of the patient, at the virtual feature, etc.), such as for display on the augmented reality display. The indication of the impingement may be displayed by the augmented reality display by changing an attribute of the virtual feature. For example, the virtual feature may be highlighted, encircled, flash, change color, be augmented by one or more additional features (e.g., highlight, circle, color change, etc.), or the like. In an example, the virtual feature may be a hip or patient anatomy in an area of a hip. In this example, the indication of the impingement may include a red circle around the hip or the area, overlaying a color on the hip or the area (i.e., making the hip or the area appear to be a different color), flashing a light at or near the hip or the area, or the like.

Figure 8:
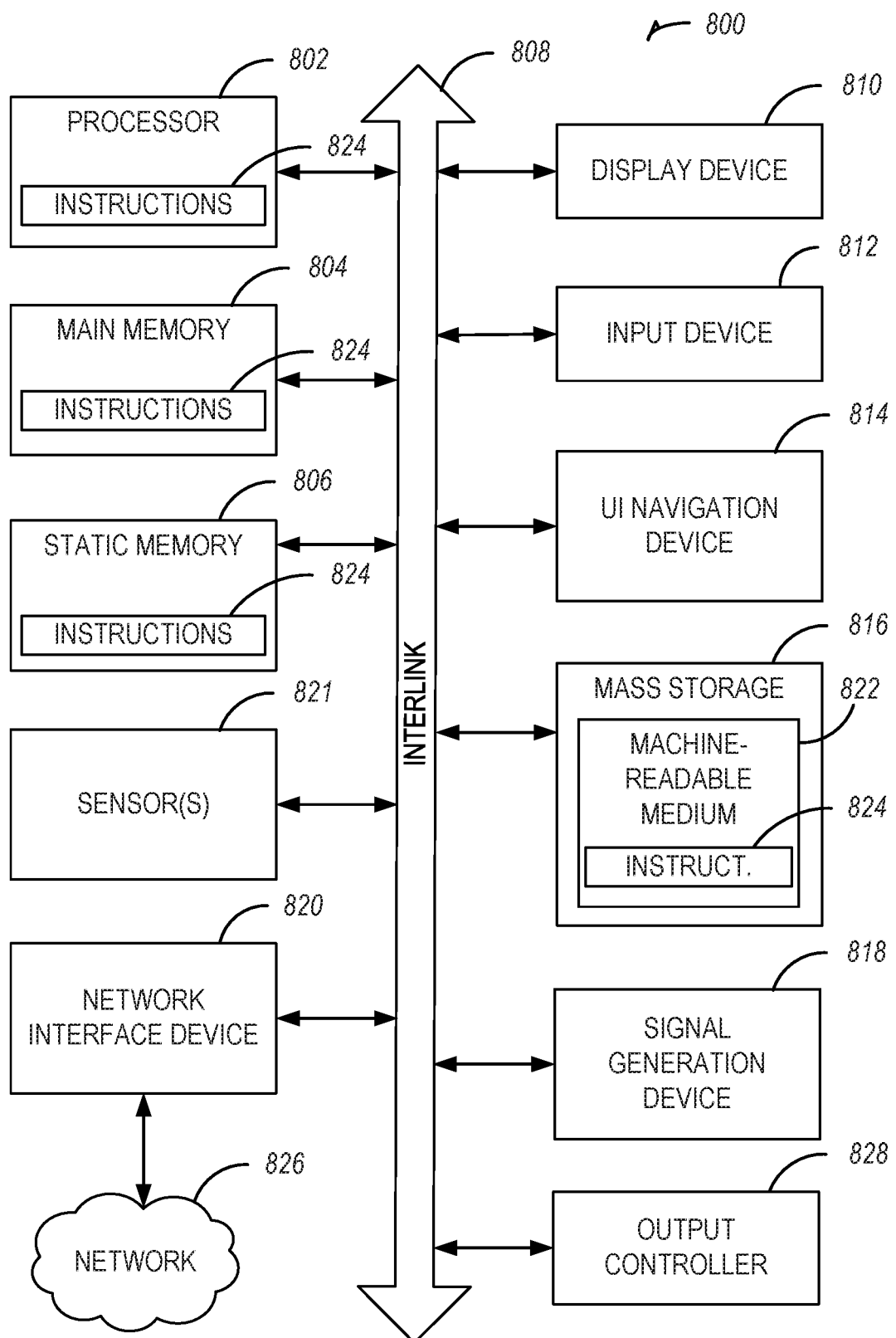
FIG. 8 illustrates generally an example of a block diagram of a machine upon which any one or more of the techniques discussed herein may perform in accordance with some embodiments.

FIG. 8 illustrates generally an example of a block diagram of a machine 800 upon which any one or more of the techniques (e.g., methodologies) discussed herein may perform in accordance with some embodiments. In alternative embodiments, the machine 800 may operate as a standalone device or may be connected (e.g., networked) to other machines. In a networked deployment, the machine 800 may operate in the capacity of a server machine, a client machine, or both in server-client network environments. The machine 800 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810, an alphanumeric input device 812 (e.g., a keyboard), and a user interface (UI) navigation device 814 (e.g., a mouse). In an example, the display unit 810, alphanumeric input device 812 and UI navigation device 814 may be a touch screen display. The display unit 810 may include goggles, glasses, or other AR or VR display components. For example, the display unit may be worn on a head of a user and may provide a heads-up-display to the user. The alphanumeric input device 812 may include a virtual keyboard (e.g., a keyboard displayed virtually in a VR or AR setting.

The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices.

The storage device 816 may include a machine readable medium 822 that is non-transitory on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine readable medium 822 is illustrated as a single medium, the term "machine readable medium" may include a single medium or multiple media (e.g., a centralized or distributed database, or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

VARIOUS NOTES & EXAMPLES

Each of these non-limiting examples may stand on its own, or may be combined in various permutations or combinations with one or more of the other examples.

Example 1 is an augmented reality device for use during patient diagnosis, comprising: an imaging device to capture a series of images of the patient; an augmented reality display to present, while permitting the patient to be viewed through the augmented reality display, a virtual feature corresponding to anatomy of the patient obtained from at least one image of the series of images; processing circuitry to: detect impingement of the anatomy of the patient based on a plurality of images from the series of images; and output, for display on the augmented reality display, an indication of the impingement at the virtual feature by changing an attribute of the virtual feature.

In Example 2, the subject matter of Example 1 includes, wherein the processing circuitry is further to create a virtual implant, based on the at least one image, and output the virtual implant for display on the augmented reality display.

In Example 3, the subject matter of Examples 1-2 includes, wherein the augmented reality device is in communication with a second augmented reality device, and wherein processing circuitry of the augmented reality device is further to output a command to control an aspect of operation of the second augmented reality device.

In Example 4, the subject matter of Example 3 includes, wherein the command causes the second augmented reality device to display fewer details in a display of the second augmented reality device than the presented in the augmented reality display of the augmented reality device.

In Example 5, the subject matter of Examples 3-4 includes, wherein the processing circuitry is further to: receive an input adjusting, moving, or changing a virtual component displayed in the augmented reality display; and output a command to cause a corresponding virtual component displayed in the second augmented reality display of the second augmented reality device to be adjusted, moved, or changed accordingly.

In Example 6, the subject matter of Examples 1-5 includes, wherein the augmented reality display is to project a virtual plane to allow a surgeon to keep the anatomy of the patient within a corresponding plane while performing a range of motion test, wherein the virtual plane is used for a biomechanical measurement used in a diagnostic exam.

In Example 7, the subject matter of Examples 1-6 includes, wherein the processing circuitry is further to receive an input manipulating the virtual feature.

In Example 8, the subject matter of Examples 1-7 includes, wherein the processing circuitry is further to: determine, from a second plurality of images from the series of images, that the anatomy of the patient has moved; and in response to the anatomy of the patient moving, determine that the impingement has resolved; and wherein, in response to determining that the impingement has resolved, the augmented reality display is to stop displaying the indication of the impingement at the virtual feature.

In Example 9, the subject matter of Examples 1-8 includes, wherein the virtual feature includes at least one of a virtual bone or set of virtual bones, a virtual implant, or a virtual skeletal model presented overlaid on the patient, the virtual skeletal model configured to move when the patient moves.

In Example 10, the subject matter of Examples 1-9 includes, wherein the augmented reality display presents one or more spinopelvic angles corresponding to the virtual feature.

Example 11 is a method for using an augmented reality device during patient diagnosis, the method comprising: capturing, using an imaging device, a series of images of the patient; presenting using an augmented reality display, while permitting the patient to be viewed through the augmented reality display, a virtual feature corresponding to anatomy of the patient obtained from at least one image of the series of images; detecting, using processing circuitry, impingement of the anatomy of the patient based on a plurality of images from the series of images; and displaying on the augmented reality display, an indication of the impingement at the virtual feature by changing an attribute of the virtual feature.

In Example 12, the subject matter of Example 11 includes, creating a virtual implant, based on the at least one image, and outputting the virtual implant for display on the augmented reality display.

In Example 13, the subject matter of Examples 11-12 includes, controlling a second augmented reality device using the processing circuitry of the augmented reality device by outputting a command to control an aspect of operation of the second augmented reality device.

In Example 14, the subject matter of Example 13 includes, wherein the command causes the second augmented reality device to display fewer details in a display of the second augmented reality device than the presented in the augmented reality display of the augmented reality device.

In Example 15, the subject matter of Examples 13-14 includes, receiving an input adjusting, moving, or changing a virtual component displayed in the augmented reality display; and outputting a command to cause a corresponding virtual component displayed in the second augmented reality display of the second augmented reality device to be adjusted, moved, or changed accordingly.

In Example 16, the subject matter of Examples 11-15 includes, projecting, using the augmented reality display, a virtual plane to allow a surgeon to keep the anatomy of the patient within a corresponding plane while performing a range of motion test, and wherein the virtual plane is used for a biomechanical measurement used in a diagnostic exam.

In Example 17, the subject matter of Examples 11-16 includes, wherein the virtual feature includes at least one of a virtual bone or set of virtual bones, a virtual implant, or a virtual skeletal model presented overlaid on the patient, the virtual skeletal model configured to move when the patient moves.

In Example 18, the subject matter of Examples 11-17 includes, determining, from a second plurality of images from the series of images, that the anatomy of the patient has moved; determining, in response to the anatomy of the patient moving, that the impingement has resolved; and in response to determining that the impingement has resolved, stop displaying the indication of the impingement at the virtual feature on the augmented reality display.

Example 19 is at least one machine-readable medium including instructions for using an augmented reality device during patient diagnosis, which when executed by a machine, cause the machine to: capture, using an imaging device, a series of images of the patient; present using an augmented reality display, while permitting the patient to be viewed through the augmented reality display, a virtual feature corresponding to anatomy of the patient obtained from at least one image of the series of images; detect, using processing circuitry, impingement of the anatomy of the patient based on a plurality of images from the series of images; and display on the augmented reality display, an indication of the impingement at the virtual feature by changing an attribute of the virtual feature.

In Example 20, the subject matter of Example 19 includes, wherein the processing circuitry is further to: determine, from a second plurality of images from the series of images, that the anatomy of the patient has moved; in response to the anatomy of the patient moving, determine that the impingement has resolved; and wherein, in response to determining that the impingement has resolved, the augmented reality display is to stop displaying the indication of the impingement at the virtual feature.

Example 21 is an augmented reality device for use during patient diagnosis, which may comprise: an imaging device to image the patient (e.g., in real time); an augmented reality display to present, while permitting the patient to be viewed through the augmented reality display, a virtual feature corresponding to anatomy of the patient obtained from the image; an impingement detection component (e.g., a processor to detect impingement from image data, a camera to detect impingement from one or more images, or a user interface to receive user input indicating impingement) to identify impingement at the virtual feature; and wherein the augmented reality display is further to present an indication of impingement at the virtual feature (e.g., by highlighting a portion of the virtual feature or changing a color of a portion of the virtual feature).

In Example 22, the subject matter of Example 21 includes, a virtual surgical implant creation system to create an implant, for example based on the image, wherein the implant may be displayed on the augmented reality display as a virtual component.

In Example 23, the subject matter of Examples 21-22 includes, wherein the augmented reality device is in communication with a second augmented reality device, the augmented reality device to control aspects of operation of the second augmented reality device (e.g., what is displayed); wherein the augmented reality device may be a surgeon's device and the second augmented reality device may be a patient's device.

In Example 24, the subject matter of Example 23 includes, wherein the patient sees less details in a display of the second augmented reality device than the surgeon sees in the augmented reality display of the augmented reality device.

In Example 25, the subject matter of Examples 23-24 includes, wherein when the surgeon adjusts, moves, or changes a virtual component displayed in the augmented reality display, a corresponding virtual component displayed in a second augmented reality display of the second augmented reality device is adjusted, moved, or changed accordingly.

In Example 26, the subject matter of Examples 21-25 includes, wherein the augmented reality display is to project a plane to allow the anatomy of the patient to be kept within the plane while performing a range of motion test (e.g., rotation, flexion, etc.).

In Example 27, the subject matter of Example 26 includes, wherein the plane is used for any biomechanical measurement that is used in a diagnostic exam (e.g., extension and rotation in the shoulder, a scoliosis diagnosis, or the like).

In Example 28, the subject matter of Examples 21-27 includes, wherein the virtual feature is created using two or more two dimensional images, for example as obtained by the imaging device.

In Example 29, the subject matter of Examples 21-28 includes, wherein the virtual feature may include a bone or set of bones; wherein the virtual feature may include an implant; or wherein the virtual feature may include a skeletal model presented overlaid on the patient that is configured to move when the patient moves (e.g., linked).

In Example 30, the subject matter of Examples 21-29 includes, wherein the augmented reality display may present a plane or axis for orientation for performing a range of motion test on the patient.

In Example 31, the subject matter of Examples 21-30 includes, wherein the augmented reality display may present one or more Spinopelvic angles corresponding to the virtual feature.

Example 32 is at least one machine-readable medium including instructions that, when executed by processing circuitry, cause the processing circuitry to perform operations to implement of any of Examples 1-31.

Example 33 is an apparatus comprising means to implement of any of Examples 1-31.

Example 34 is a system to implement of any of Examples 1-31.

Example 35 is a method to implement of any of Examples 1-31.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. An augmented reality device for use during patient diagnosis, comprising:

an imaging device to capture a series of images of the patient;

an augmented reality display to present, while permitting the patient to be viewed through the augmented reality display, a virtual anatomical feature of the patient obtained from at least one image of the series of images, and to present one or more changing spinopelvic angles corresponding to the virtual anatomical feature while performing a range of motion test;

processing circuitry to:

detect impingement of the anatomy of the patient based on a plurality of images from the series of images; and output, for display on the augmented reality display, an indication of the impingement at the virtual anatomical feature by changing an attribute of the virtual anatomical feature.

2. The augmented reality device of claim 1, wherein the processing circuitry is further to create a virtual implant, based on the at least one image, and output the virtual implant for display on the augmented reality display.

3. The augmented reality device of claim 1, wherein the augmented reality device is in communication with a second augmented reality device, and wherein processing circuitry of the augmented reality device is further to output a command to control an aspect of operation of the second augmented reality device.

4. The augmented reality device of claim 3, wherein the command causes the second augmented reality device to display fewer details in a display of the second augmented reality device than the presented in the augmented reality display of the augmented reality device.

5. The augmented reality device of claim 3, wherein the processing circuitry is further to:

receive an input adjusting, moving, or changing a virtual component displayed in the augmented reality display; and output a command to cause a corresponding virtual component displayed in the second augmented reality display of the second augmented reality device to be adjusted, moved, or changed accordingly.

6. The augmented reality device of claim 1, wherein the augmented reality display is to project a virtual plane to allow a surgeon to keep the anatomy of the patient within a corresponding plane while performing the range of motion test, wherein the virtual plane is used for a biomechanical measurement used in a diagnostic exam.

7. The augmented reality device of claim 1, wherein the processing circuitry is further to receive an input manipulating the virtual anatomical feature.

8. The augmented reality device of claim 1, wherein the processing circuitry is further to:

determine, from a second plurality of images from the series of images, that the anatomy of thy: patient has moved; and in response to the anatomy of the patient moving, determine that the impingement has resolved; and wherein, in response to determining that the impingement has resolved, the augmented reality display is to stop displaying the indication of the impingement at the virtual anatomical feature.

9. The augmented reality device of claim 1, wherein the virtual anatomical feature includes at least one of a virtual bone or set of virtual bones or a virtual skeletal model presented overlaid on the patient, the virtual anatomical feature configured to move when the patient moves.

10. A method for using an augmented reality device during patient diagnosis, the method comprising:

capturing, using an imaging device, a series of images of the patient;

presenting using an augmented reality display, while permitting the patient to be viewed through the augmented reality display, a virtual anatomical feature of the patient obtained from at least one image of the series of images and one or more changing spinopelvic angles corresponding to the virtual anatomical feature while performing a range of motion test;

detecting, using processing circuitry, impingement of the anatomy of the patient based on a plurality of images from the series of images; and displaying on the augmented reality display, an indication of the impingement at the virtual anatomical feature by changing an attribute of the virtual anatomical feature.

11. The method of claim 10, further comprising creating a virtual implant, based on the at least one image, and outputting the virtual implant for display on the augmented reality display.

12. The method of claim 10, further comprising controlling a second augmented reality device using the processing circuitry of the augmented reality device by outputting a command to control an aspect of operation of the second augmented reality device.

13. The method of claim 12, wherein the command causes the second augmented reality device to display fewer details in a display of the second augmented reality device than the presented in the augmented reality display of the augmented reality device.

14. The method of claim 12, further comprising:
receiving an input adjusting, moving, or changing a virtual component displayed in the augmented reality display; and
outputting a command to cause a corresponding virtual component displayed in the second augmented reality display of the second augmented reality device to be adjusted, moved, or changed accordingly.

15. The method of claim 10, further comprising projecting, using the augmented reality display, a virtual plane to allow a surgeon to keep the anatomy of the patient within a corresponding plane while performing the range of motion test, and wherein the virtual plane is used for a biomechanical measurement used in a diagnostic exam.

16. The method of claim 10, wherein the virtual anatomical feature includes at least one of a virtual bone or set of virtual bones or a virtual skeletal model presented overlaid on the patient, the virtual anatomical feature configured to move when the patient moves.

17. The method of claim 10, further comprising
determining, from a second plurality of images from the series of images, that the anatomy of the patient has moved;
determining, in response to the anatomy of the patient moving, that the impingement has resolved; and
in response to determining that the impingement has resolved, stop displaying the indication of the impingement at the virtual anatomical feature on the augmented reality display.

18. At least one non-transitory machine-readable medium including instructions for using an augmented reality device during patient diagnosis, which when executed by a machine, cause the machine to:
capture, using an imaging device, a series of images of the patient;
present using an augmented reality display, while permitting the patient to be viewed through the augmented reality display, a virtual anatomical feature of the patient obtained from at least one image of the series of images, and present one or more changing spinopelvic angles corresponding to the virtual anatomical feature while performing a range of motion test;
detect, using processing circuitry, impingement of the anatomy of the patient based on a plurality of images from the series of images; and
display on the augmented reality display, an indication of the impingement at the virtual anatomical feature by changing an attribute of the virtual anatomical feature.

19. The at least one non-transitory machine-readable medium of claim 18, wherein the processing circuitry is further to:
determine; from a second plurality of images from the series of images, that the anatomy of the patient has moved;
in response to the anatomy of the patient moving, determine that the impingement has resolved; and
wherein, in response to determining that the impingement has resolved, the augmented reality display is to stop displaying the indication of the impingement at the virtual anatomical feature.

* * * * *